US009434657B2

United States Patent
Onishi et al.

(10) Patent No.: US 9,434,657 B2
(45) Date of Patent: Sep. 6, 2016

(54) HYDROCARBON SYNTHESIS REACTION APPARATUS, START-UP PROCESS THEREOF, AND HYDROCARBON SYNTHESIS REACTION SYSTEM

(75) Inventors: Yasuhiro Onishi, Tokyo (JP); Kazuhiko Tasaka, Yokohama (JP); Tomoyuki Mikuriya, Kawasaki (JP)

(73) Assignees: Japan Oil, Gas and Metals National Corporation, Tokyo (JP); INPEX CORPORATION, Tokyo (JP); JX Nippon Oil & Energy Corporation, Tokyo (JP); Japan Petroleum Exploration Co., Ltd, Tokyo (JP); COSMO OIL CO., LTD., Tokyo (JP); NIPPON STEEL & SUMIKIN ENGINEERING CO., LTD, Tokyo (JP)

( * ) Notice: Subject to any disclaimer, the term of this patent is extended or adjusted under 35 U.S.C. 154(b) by 498 days.

(21) Appl. No.: 14/006,998

(22) PCT Filed: Mar. 13, 2012

(86) PCT No.: PCT/JP2012/056399
§ 371 (c)(1),
(2), (4) Date: Sep. 24, 2013

(87) PCT Pub. No.: WO2012/132876
PCT Pub. Date: Oct. 4, 2012

(65) Prior Publication Data
US 2014/0135410 A1    May 15, 2014

(30) Foreign Application Priority Data
Mar. 30, 2011    (JP) .................. 2011-076649

(51) Int. Cl.
| C07C 1/00 | (2006.01) |
| C07C 1/02 | (2006.01) |
| C07C 1/04 | (2006.01) |
| C10G 2/00 | (2006.01) |
| B01J 8/00 | (2006.01) |

(Continued)

(52) U.S. Cl.
CPC .............. *C07C 1/041* (2013.01); *B01J 8/1809* (2013.01); *B01J 8/22* (2013.01); *B01J 19/0013* (2013.01);

(Continued)

(58) Field of Classification Search
CPC . C07C 1/00–1/041; C10G 2/00; C10G 2/30; C10G 2/32; C10G 2/34; C10G 2/342; C10G 2300/40; C10G 2300/4031; C10G 2300/408; B01J 8/00; B01J 8/18; B01J 8/1809; B01J 8/20; B01J 8/22; B01J 19/00; B01J 19/0006; B01J 19/0013; B01J 19/0033; B01J 19/24; B01J 2208/00–2208/00044; B01J 2208/00061; B01J 2208/00106; B01J 2208/00265; B01J 2208/00274; B01J 2208/00548; B01J 2208/00628; B01J 2208/00646; B01J 2219/00049; B01J 2219/00191–2219/00195; B01J 2219/00202; B01J 2219/00211; B01J 2219/00213; B01J 2219/00222; B01J 2219/00227; B01J 2219/00229; B01J 2219/00231; B01J 2219/00238
See application file for complete search history.

(56) References Cited

U.S. PATENT DOCUMENTS

| 6,838,487 B1 | 1/2005 | Demirel et al. |
| 2005/0113466 A1 | 5/2005 | Guillard et al. |

(Continued)

FOREIGN PATENT DOCUMENTS

| CN | 101970344 A | 2/2011 |
| EP | 2351815 A1 | 8/2011 |

(Continued)

OTHER PUBLICATIONS

Notice of Allowance issued Jan. 19, 2016 in JP Application No. 2011076649.

(Continued)

*Primary Examiner* — Natasha Young
(74) *Attorney, Agent, or Firm* — Panitch Schwarze Belisario & Nadel LLP

(57) ABSTRACT

The hydrocarbon synthesis reaction apparatus is provided with a synthesis gas supply line in which a synthesis gas is compressed and supplied by a first compressor, a reactor configured to accommodate a catalyst slurry, a gas-liquid separator configured to separate an unreacted synthesis gas and hydrocarbons discharged from the reactor into a gas and a liquid, a first recycle line in which the unreacted synthesis gas after separation into a gas and a liquid is compressed and recycled into the reactor by a second compressor, and a second recycle line configured to recycle a residual unreacted synthesis gas after separation into a gas and a liquid into the inlet side of the first compressor at the time of start-up operation when the synthesis gas is gradually increased in the amount to be introduced.

5 Claims, 5 Drawing Sheets

(51) Int. Cl.
  *B01J 8/18*   (2006.01)
  *B01J 8/20*   (2006.01)
  *B01J 8/22*   (2006.01)
  *B01J 19/00*  (2006.01)
  *B01J 19/24*  (2006.01)

(52) U.S. Cl.
  CPC ............ *B01J 19/0033* (2013.01); *C10G 2/342* (2013.01); *B01J 2208/00061* (2013.01); *B01J 2208/00274* (2013.01); *B01J 2208/00548* (2013.01); *B01J 2208/00646* (2013.01); *B01J 2219/00202* (2013.01); *B01J 2219/00213* (2013.01); *B01J 2219/00231* (2013.01); *B01J 2219/00238* (2013.01); *C10G 2300/4031* (2013.01); *C10G 2300/4081* (2013.01)

(56) References Cited

U.S. PATENT DOCUMENTS

| | | |
|---|---|---|
| 2008/0275144 A1 | 11/2008 | Van Hardeveld et al. |
| 2011/0152593 A1* | 6/2011 | Kelly .................. C10G 3/49 585/319 |
| 2012/0190535 A1 | 7/2012 | Onishi et al. |

FOREIGN PATENT DOCUMENTS

| | | |
|---|---|---|
| EP | 2474594 A1 | 7/2012 |
| JP | 2005-517698 A | 6/2005 |
| JP | 2010-083998 A | 4/2010 |
| JP | 5501365 B2 | 5/2014 |
| WO | 03068715 A1 | 8/2003 |
| WO | WO 2004/026994 A1 * | 4/2004 |
| WO | 2010038399 A1 | 4/2010 |
| WO | 2011024651 A1 | 3/2011 |
| WO | 2011024652 A1 | 3/2011 |

OTHER PUBLICATIONS

Extended European Search Report issued Dec. 8, 2014 in EP Application No. 12763512.6.

Office Action issued Sep. 23, 2014 in CN Application No. 201280015171.0.

Int'l Search Report issued Apr. 24, 2012 in Int'l Application No. PCT/JP2012/056399.

* cited by examiner

US 9,434,657 B2

HYDROCARBON SYNTHESIS REACTION APPARATUS, START-UP PROCESS THEREOF, AND HYDROCARBON SYNTHESIS REACTION SYSTEM

CROSS-REFERENCE TO RELATED APPLICATION

This application is a Section 371 of International Application No. PCT/JP2012/056399, filed Mar. 13, 2012, which was published in the Japanese language on Oct. 4, 2012, under International Publication No. WO 2012/132876 A1, which claims priority to Japanese Patent Application No. JP 2011-076649, filed Mar. 30, 2011, and the disclosure of which is incorporated herein by reference.

BACKGROUND OF THE INVENTION

1. Field of the Invention

The present invention relates to a hydrocarbon synthesis reaction apparatus, a start-up process thereof, and a hydrocarbon synthesis reaction system.

Priority is claimed on Japanese Patent Application No. 2011-076649 filed on Mar. 30, 2011, the content of which is incorporated herein by reference.

2. Description of Related Art

In recent years, as a process for synthesizing liquid fuels from natural gas, the GTL (Gas To Liquids: liquid fuels synthesis) technique has been developed. This GTL technique includes the steps of reforming a natural gas to produce a synthesis gas containing carbon monoxide gas (CO) and hydrogen gas ($H_2$) as main components, synthesizing hydrocarbons using this synthesis gas as a feedstock gas and using a catalyst via the Fischer-Tropsch synthesis reaction (hereinafter also referred to as the "FT synthesis reaction"), and then hydrogenating and fractionating these hydrocarbons to produce liquid fuel products such as naphtha (raw gasoline), kerosene, gas oil and wax and the like.

In the hydrocarbon synthesis reaction apparatus used in this GTL technique, the hydrocarbons are synthesized by subjecting the carbon monoxide gas and hydrogen gas within the synthesis gas to an FT synthesis reaction inside a reactor main unit that contains a slurry prepared by suspending solid catalyst particles (such as a cobalt catalyst or the like) in a liquid medium (for example, liquid hydrocarbons or the like).

FIG. 7 shows a schematic constitution of a conventional hydrocarbon synthesis reaction apparatus.

This hydrocarbon synthesis reaction apparatus is provided with a synthesis gas supply line 31 in which a synthesis gas containing a carbon monoxide gas and a hydrogen gas as main components is sent by a synthesis gas sending device 3 and the thus sent synthesis gas (SG) is compressed and supplied by a first compressor 34; a reactor 30 which accommodates a catalyst slurry prepared by suspending solid catalyst particles in a liquid to synthesize hydrocarbons by bringing the synthesis gas supplied from the synthesis gas supply line 31 into contact with the catalyst slurry; a gas-liquid separator 38 which separates an unreacted synthesis gas and hydrocarbons discharged from the reactor 30 into a gas and a liquid; an off-gas discharge line 37 which discharges a portion of gas after separation by the gas-liquid separator 38 as an off gas outside a system; a recycle line 32 in which the unreacted synthesis gas after separation by the gas-liquid separator 38 is compressed and recycled into the reactor 30 by a second compressor 35.

A hydrocarbon synthesis reaction apparatus which is provided with the above-described recycle line has been disclosed in Patent Document 1, for example.

Where this type of hydrocarbon synthesis reaction apparatus is used to start-up a system, first, prior to introduction of a synthesis gas, nitrogen, which is an inert gas, is blown in advance into the system for securing gas replacement inside the system and fluidity inside the reactor 30, and the nitrogen is cycled via the recycle line 32. In this case, cycle operation is carried out in a state that the nitrogen to be cycled is secured at a substantial amount. A catalyst slurry inside the reactor is kept in a fluid state by cycling a nitrogen gas and, thereafter, the nitrogen gas is gradually replaced with the synthesis gas. While the synthesis gas amount is kept lower in flow rate (for example, 70%) which is lower than a rated flow rate, the reactor 30 is increased in temperature to raise reactivity (conversion rate). Thereby, the synthesis gas introduced in an amount of up to 100% loads up to shift to operation at a rated flow rate, while confirming stable reaction conditions.

CITATION LIST

Patent Document

Patent Document 1: Japanese Translation of International Application No. 2005-517698

SUMMARY OF THE INVENTION

Problem to be Solved

However, according to the above-described process, the flow rate of gas which flows into the reactor 30 is a low flow rate which will not reach 100% of the rated gas flow rate, by which the slurry inside the reactor 30 is not favorably agitated and is made unstable, by which it is impossible to rapidly improve the reactivity (conversion rate). This has been a problem.

Further, there has been another problem that a long start-up time is required for shifting from the cycling of nitrogen to operation at a rated flow rate.

The present invention has been made in view of the above situation, an object of which is to provide a hydrocarbon synthesis reaction apparatus which is capable of starting up a system in a short period of time, while securing a stable fluid state of catalyst and reaction conditions, and also to provide a start-up process thereof and a hydrocarbon synthesis reaction system.

Means for Solving the Problem

The hydrocarbon synthesis reaction apparatus of the present invention is provided with a synthesis gas supply line in which a synthesis gas containing a carbon monoxide gas and a hydrogen gas as main components is sent by a synthesis gas sending device and the thus sent synthesis gas is compressed and supplied by a first compressor; a reactor configured to accommodate a catalyst slurry prepared by suspending solid catalyst particles in a liquid to synthesize hydrocarbons by bringing the synthesis gas supplied from the synthesis gas supply line into contact with the catalyst slurry; a gas-liquid separator configured to separate an unreacted synthesis gas and hydrocarbons discharged from the reactor into a gas and a liquid; an off-gas discharge line configured to discharge a portion of gas after separation by the gas-liquid separator as an off gas outside a system; a first recycle line in which the unreacted synthesis gas after separation by the gas-liquid separator is compressed and recycled into the reactor by a second compressor; and a second recycle line configured to recycle into the inlet side of the first compressor a residual unreacted synthesis gas to be introduced into the first recycle line, a part of the unreacted synthesis gas after separation by the gas-liquid separator, at the time of start-up operation when the synthesis gas to be introduced from the synthesis gas sending device to the reactor is introduced in a gradually increasing amount from a processing flow rate lower than the processing flow rate of the synthesis gas to be processed during operation at a rated flow rate to a processing flow rate of the synthesis gas during operation at a rated flow rate.

The hydrocarbon synthesis reaction apparatus of the present invention is provided with the first recycle line and an inert gas flow line which is communicated with the inlet side of the first compressor from the gas-liquid separator as an inert gas flow line in which a gas inside a system is replaced with an inert gas at the time of starting up the reactor and the catalyst slurry is also fluidized. In addition, the inert gas flow line may also be used as the second recycle line.

The hydrocarbon synthesis reaction apparatus of the present invention may be further provided with a converging and mixing unit which is installed at an upstream side at a site where the synthesis gas sent from the synthesis gas sending device is introduced into the inlet side of the first compressor and in which the unreacted synthesis gas from the second recycle line is converged and mixed with the synthesis gas sent from the synthesis gas sending device; and a temperature controlling device configured to control a mixed gas mixed by the converging and mixing unit in such a manner that a temperature thereof is made at least equal to or higher than a temperature of the unreacted synthesis gas from the second recycle line.

The hydrocarbon synthesis reaction system of the present invention is for producing a liquid fuel base stock from a hydrocarbon feedstock. This system is provided with the hydrocarbon synthesis reaction apparatus and a product fractionating unit configured to fractionate a liquid fuel base stock from hydrocarbons produced by the hydrocarbon synthesis reaction apparatus. The synthesis gas sending device is a synthesis gas production unit configured to reform the hydrocarbon feedstock to produce the synthesis gas and sends the synthesis gas to the synthesis gas supply line.

The start-up process of the hydrocarbon synthesis reaction apparatus of the present invention is for a hydrocarbon synthesis reaction apparatus which is provided with: a synthesis gas supply line in which a synthesis gas containing carbon monoxide gas and hydrogen gas as main components is sent by a synthesis gas sending device and the thus sent synthesis gas is compressed and supplied by a first compressor; a reactor configured to accommodate a catalyst slurry prepared by suspending solid catalyst particles in a liquid to synthesize hydrocarbons by bringing the synthesis gas supplied from the synthesis gas supply line into contact with the catalyst slurry; a gas-liquid separator configured to separate an unreacted synthesis gas and hydrocarbons discharged from the reactor into a gas and a liquid; an off-gas discharge line configured to discharge a portion of gas after separation by the gas-liquid separator as an off gas outside a system; a first recycle line in which the unreacted synthesis gas after separation by the gas-liquid separator is compressed and recycled into the reactor by a second compressor; and a second recycle line which is communicated with the inlet side of the first compressor from the gas-liquid separator. This start-up process includes a first step in which, prior to introduction of the synthesis gas into the reactor, an inert gas is in advance introduced into the reactor through the synthesis gas supply line, the first compressor and the second compressor are both operated at a rated flow rate to flow the inert gas via the first recycle line and the second recycle line, thereby, a gas inside a system is replaced with the inert gas, with the off gas discharged from the off-gas discharge line, and also the catalyst slurry is fluidized; a second step in which the synthesis gas is introduced through the synthesis gas supply line, in a state with the first compressor operated at a rated flow rate, into the reactor which is in a state that the catalyst slurry is fluidized by performing the first step at a flow rate lower than a processing flow rate during operation at a rated flow rate, the unreacted synthesis gas discharged from the reactor and separated by the gas-liquid separator is flowed via the first recycle line by operating the second compressor at a rated flow rate, and also a residual unreacted synthesis gas to be introduced into the first recycle line, a part of the unreacted synthesis gas after separation by the gas-liquid separator, is flowed via the second recycle line to the inlet side of the first compressor operated at a rated flow rate, thereby, the gas inside the system is replaced with the synthesis gas, with the off gas discharged from the off-gas discharge line, and the flow rate of supplying the synthesis gas from the synthesis gas supply line is also maintained at a constant flow rate lower than a processing flow rate during operation at a rated flow rate; and a third step in which, at a stage where reaction becomes stable in the second step, the synthesis gas to be introduced into the reactor through the synthesis gas supply line is gradually increased in flow rate, while the unreacted synthesis gas to be flowed through the second recycle line is gradually decreased in flow rate, and the flow rate of the synthesis gas to be finally introduced into the reactor through the synthesis gas supply line is increased up to the processing flow rate of the synthesis gas which is processed during operation at a rated flow rate.

Advantageous Effects of the Invention

According to the present invention, at the time of start-up operation when an introduction amount of the synthesis gas to be introduced into the reactor is required to be gradually increased from a low flow rate confirmed the safety thereof in advance to a rated flow rate, while confirming that the reaction proceeds stably, the unreacted synthesis gas can be introduced through the second recycle line into the inlet side of the first compressor for compressing the synthesis gas. Therefore, it is possible to supplement a flow rate shortage with respect to a rated flow rate of the synthesis gas upon operation of the first compressor at a rated flow rate by using the unreacted synthesis gas. That is, for example, in the start-up operation in which there is no choice but to introduce the synthesis gas at a low flow rate at the beginning, for the purpose of preventing the reaction from going out of control, the first compressor is operated at a rated flow rate to introduce a mixed gas containing the synthesis gas and the unreacted synthesis gas into the reactor at a rated flow rate. Thereby, it is possible to maintain a stable fluid state inside the reactor. Accordingly, with substantially no consideration given to influences of the fluid state, the reactor is gradually increased in temperature, by which the reactivity (conversion rate) can be raised and the flow rate of the synthesis gas can also be increased safely to a rated flow rate.

Further, at the time of start-up, prior to introduction of the synthesis gas into the reactor, the gas inside the system is replaced with an inert gas. The inert gas is flowed via the second recycle line at a rated flow rate of the first compressor, by which the shift can be made to introduction of the synthesis gas as a next stage, with a fluid state inside the reactor kept stable. Thus, events which require care and monitoring at the time of start-up are decreased to facilitate the operation. Further, the fluid state inside the reactor can be kept constant, thus making it possible to shorten the period of time necessary for shifting to stable operation at a rated flow rate. Still further, since the first compressor for compressing the synthesis gas can be fully utilized for its performance without operation at a low flow rate, it is possible to increase efficiency.

According to the present invention, the flow line which is used as a flow line of the inert gas is also used as the second recycle line through which the unreacted synthesis gas flows. It is, therefore, possible to utilize facilities to the maximum extent and also to suppress increased costs.

According to the present invention, it is possible to prevent any trouble which will be caused due to the fact that a trace amount of oil content contained in the unreacted synthesis gas undergoes condensation during recycle operation of the unreacted synthesis gas. As a result, it is possible to guarantee stable operation of the first compressor.

According to the present invention, the step of reforming a hydrocarbon feedstock to produce a synthesis gas, the step of allowing the synthesis gas to react, thereby producing hydrocarbons, and the step of fractionating a liquid fuel base stock from the hydrocarbons can be carried out sequentially. It is, thereby, possible to stably produce the liquid fuel base stock which is a final product.

According to the present invention, the inert gas can be flowed at the time of start-up via the second recycle line by operating the first compressor at a rated flow rate. Thereby, the shift can be made to introduction of the synthesis gas as a next stage, with a fluid state inside the reactor kept stable. Further, when and after the shift has been made to introduction of the synthesis gas, the first compressor is operated at a rated flow rate, by which a mixed gas containing the synthesis gas and the unreacted synthesis gas can be introduced into the reactor at a rated flow rate. Thus, it is possible to maintain a stable fluid state inside the reactor. Accordingly, with substantially no consideration given to influences of the fluid state, the reactor is gradually increased in temperature, by which the reactivity (conversion rate) can be raised and the flow rate of the synthesis gas can also be safely increased up to a rated flow rate. Therefore, events which require care and monitoring at the time of start-up are decreased to facilitate the operation.

Further, the fluid state inside the reactor can be kept constant, thus making it possible to shorten a period of time necessary for shifting to stable operation at a rated flow rate. Still further, since the first compressor for compressing the synthesis gas can be fully utilized for its performance without operation at a low flow rate, it is possible to increase the efficiency.

DETAILED DESCRIPTION OF THE INVENTION

Hereinafter, a description will be given of one embodiment of the hydrocarbon synthesis reaction system including the hydrocarbon synthesis reaction apparatus of the present invention with reference to the drawings.

(Liquid Fuel Synthesizing System)

Figure 1:
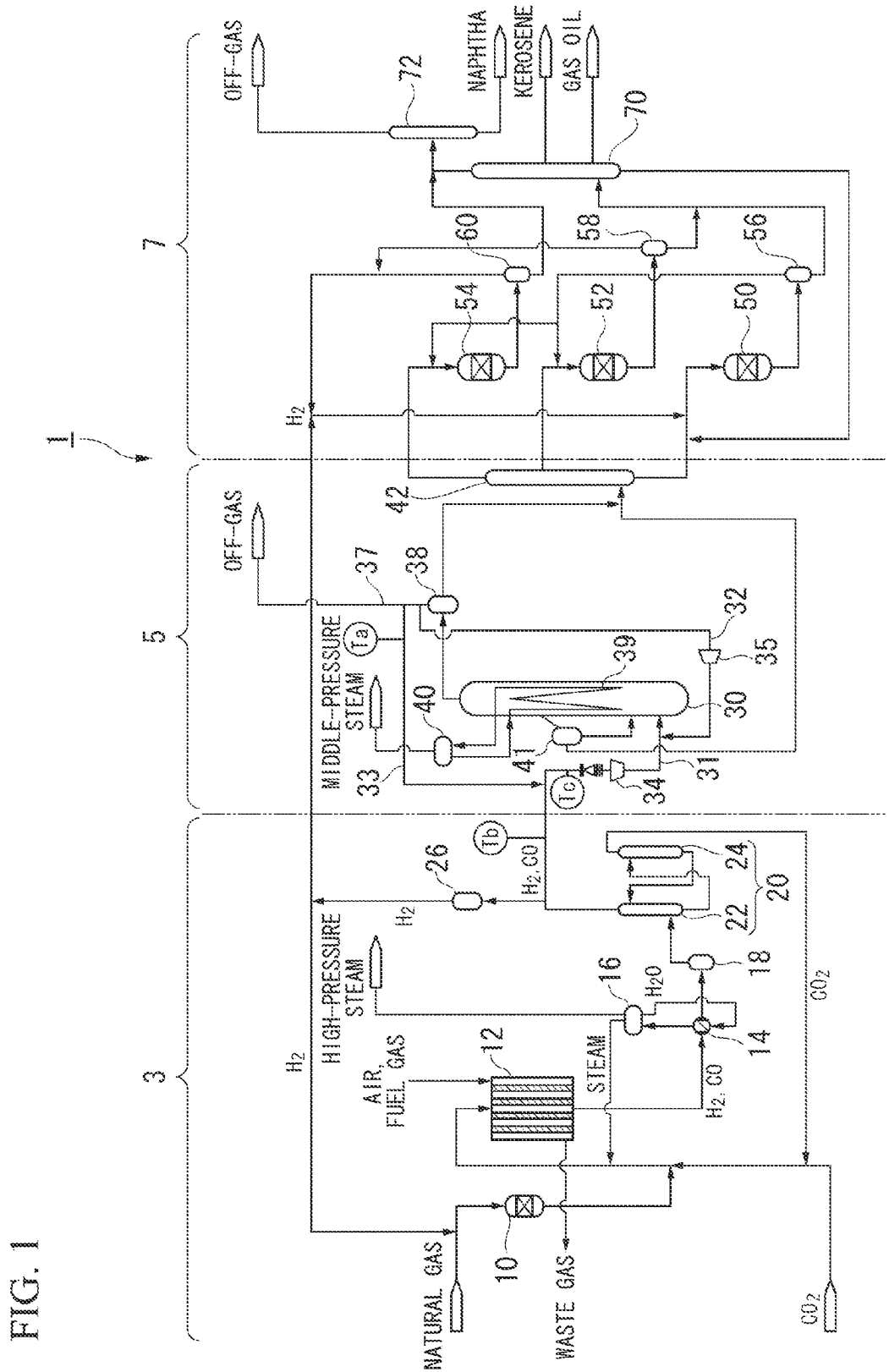
FIG. 1 is a systematic diagram which shows an entire constitution of a liquid fuel synthesizing system including one embodiment of the present invention.

As illustrated in FIG. 1, the liquid fuel synthesizing system (hydrocarbon synthesis reaction system) 1 is a plant facility which carries out a GTL process that converts a hydrocarbon feedstock such as a natural gas into liquid fuels. This liquid fuel synthesizing system 1 includes a synthesis gas production unit 3, an FT synthesis unit (hydrocarbon synthesis reaction apparatus) 5, and an upgrading unit 7. The synthesis gas production unit 3 reforms a natural gas that functions as a hydrocarbon feedstock to produce a synthesis gas containing carbon monoxide gas and hydrogen gas. The FT synthesizing unit 5 produces liquid hydrocarbon compounds from the produced synthesis gas via the FT synthesis reaction. The upgrading unit 7 hydrotreats the liquid hydrocarbon compounds synthesized by the FT synthesis reaction to produce liquid fuels and other products (such as naphtha, kerosene, gas oil, and wax). Structural elements of each of these units are described below.

First is a description of the synthesis gas production unit 3.

The synthesis gas production unit 3 is, for example, composed mainly of a desulfurization reactor 10, a reformer 12, a waste heat boiler 14, gas-liquid separators 16 and 18, a $CO_2$ removal unit 20, and a hydrogen separator 26. The desulfurization reactor 10 is composed of a hydrodesulfurizer and the like, and removes sulfur components from the natural gas that functions as the feedstock. The reformer 12 reforms the natural gas supplied from the desulfurization reactor 10 to produce a synthesis gas containing carbon monoxide gas (CO) and hydrogen gas ($H_2$) as main components. The waste heat boiler 14 recovers waste heat from the synthesis gas produced in the reformer 12 to generate a high-pressure steam. The gas-liquid separator 16 separates the water that has been heated by heat exchange with the synthesis gas in the waste heat boiler 14 into a gas (high-pressure steam) and a liquid. The gas-liquid separator 18 removes a condensed component from the synthesis gas that has been cooled in the waste heat boiler 14, and supplies a gas component to the $CO_2$ removal unit 20. The $CO_2$ removal unit 20 has an absorption tower (second absorption tower) 22 and a regeneration tower 24. The absorption tower 22 uses an absorbent to absorb carbon dioxide gas contained in the synthesis gas supplied from the gas-liquid separator 18. The regeneration tower 24 strips the carbon dioxide gas absorbed by the absorbent, thereby regenerating the absorbent. The hydrogen separator 26 separates a portion of the hydrogen gas contained in the synthesis gas from which the carbon dioxide gas has already been separated by the $CO_2$ removal unit 20. In some cases, the above $CO_2$ removal unit 20 may not need to be provided.

In the reformer 12, for example, by utilizing a steam and carbon dioxide gas reforming method represented by the chemical reaction formulas (1) and (2) shown below, the natural gas is reformed by carbon dioxide and steam, and a high-temperature synthesis gas is produced which includes carbon monoxide gas and hydrogen gas as main components. However, the reforming method employed in the reformer 12 is not limited to this steam and carbon dioxide gas reforming method. For example, a steam reforming method, a partial oxidation reforming method (PDX) using oxygen, an autothermal reforming method (ATR) that is a combination of a partial oxidation reforming method and a steam reforming method, or a carbon dioxide gas reforming method and so on, may also be used.

$$CH_4+H_2O \rightarrow CO+3H_2 \quad (1)$$

$$CH_4+CO_2 \rightarrow 2CO+2H_2 \quad (2)$$

The hydrogen separator 26 is provided on a branch line that branches off a main line which connects the $CO_2$ removal unit 20 or the gas-liquid separator 18 with a slurry bubble column reactor 30. This hydrogen separator 26 may be composed of, for example, a hydrogen PSA (Pressure Swing Adsorption) apparatus, that performs adsorption and desorption of hydrogen by utilizing a pressure difference. This hydrogen PSA apparatus has adsorbents (such as a zeolitic adsorbent, activated carbon, alumina or silica gel) packed inside a plurality of adsorption towers (not shown in the drawing) that are arranged in parallel. By sequentially repeating each of the steps of hydrogen pressurization, adsorption, desorption (depressurization) and purging within each of these adsorption towers, the hydrogen PSA apparatus can continuously supply a high-purity hydrogen gas (of approximately 99.999% purity, for example) that has been separated from the synthesis gas.

The hydrogen gas separating method employed in the hydrogen separator 26 is not limited to the type of pressure swing adsorption method utilized by the above hydrogen PSA apparatus, and for example, a hydrogen storing alloy adsorption method, a membrane separation method, or a combination thereof may also be used.

The hydrogen storing alloy method is a technique for separating hydrogen gas using, for example, a hydrogen storing alloy (such as TiFe, LaNi$_5$, TiFe$_{(0.7\ to\ 0.9)}$Mn$_{(0.3\ to\ 0.1)}$, or TiMn$_{1.5}$) that exhibits hydrogen adsorption and strip properties upon cooling and heating respectively. In the hydrogen storing alloy method, for example, hydrogen adsorption by cooling the hydrogen storing alloy, and hydrogen strip by heating the hydrogen storing alloy may be repeated alternately within a plurality of adsorption towers containing the hydrogen storing alloy. In this manner, hydrogen gas contained in the synthesis gas can be separated and recovered.

The membrane separation method is a technique that uses a membrane composed of a polymer material such as an aromatic polyimide to separate hydrogen gas, which exhibits superior membrane permeability, from a mixed gas. Since the membrane separation method does not require a phase change of the separation target materials in order to achieve separation, less energy is required for the separation operation, meaning the running costs are low. Further, because the structure of a membrane separation device is simple and compact, the facility costs are low and the surface area required to install the facility is small. Moreover, there is no driving device in a separation membrane and the stable operating range is broad, which offers another advantage in that maintenance is comparatively easy.

Next is a description of the FT synthesis unit 5.

The FT synthesis unit 5 mainly includes, for example, the reactor 30, a gas-liquid separator 40, a separator 41, a gas-liquid separator 38, a first fractionator 42. The reactor 30 uses the FT synthesis reaction to synthesize liquid hydrocarbon compounds from the synthesis gas produced by the aforementioned synthesis gas production unit 3, that is, from carbon monoxide gas and hydrogen gas. The gas-liquid separator 40 separates water that has been heated by passage through a heat transfer tube 39 disposed inside the reactor 30 into steam (middle-pressure steam) and a liquid. The separator 41 is connected to the middle section of the reactor 30, and separates the catalyst and the liquid hydrocarbon compounds. The gas-liquid separator 38 is connected to the top of the reactor 30 to cool an unreacted synthesis gas and gaseous hydrocarbon compounds, thereby separating the liquid hydrocarbon compounds and a gas which contains the unreacted synthesis gas. This gas contains unnecessary components such as methane inside a system and, therefore, a portion of the gas is discharged as an off gas from the off-gas discharge line 37 outside the system. The first fractionator 42 fractionally distills the liquid hydrocarbon compounds that have been supplied from the reactor 30 via the separator 41 and the gas-liquid separator 38 into a series of fractions.

The reactor 30 is an example of a reactor that synthesizes liquid hydrocarbon compounds from a synthesis gas, and functions as an FT synthesis reactor that synthesizes liquid hydrocarbon compounds from the synthesis gas by the FT synthesis reaction. The reactor 30 is formed, for example, from a bubble column slurry bed type reactor in which a slurry composed mainly of catalyst particles and an oil medium (liquid medium, liquid hydrocarbons) is contained inside a column type vessel. This reactor 30 synthesizes gaseous or liquid hydrocarbon compounds from the synthesis gas by the FT synthesis reaction. Specifically, in the reactor 30, a synthesis gas that represents the feedstock gas is supplied as gas bubbles from a sparger positioned in the bottom of the reactor 30, and these gas bubbles pass through the slurry, which has been formed by suspending catalyst particles in the oil medium. In this suspended state, the hydrogen gas and carbon monoxide gas contained in the synthesis gas react with each other to synthesize hydrocarbon compounds, as shown in the following chemical reaction formula (3).

$$2nH_2+nCO \rightarrow -(CH_2)_n-+nH_2O \quad (3)$$

Here, in the above-described reaction, a percentage of carbon monoxide gas which has been consumed inside the reactor with respect to the carbon monoxide gas (CO) supplied to the FT synthesis unit 5 is referred to as the "CO conversion rate" herein. This CO conversion rate is calculated in percentage by a molar flow rate of carbon monoxide gas in gas which flows into the FT synthesis unit 5 per unit time (synthesis gas-to-CO molar flow rate) and a molar flow rate of carbon monoxide gas in off gas drawn out per unit time through the off-gas discharge line 37 from the FT synthesis unit 5 (off gas-to-CO molar flow rate). That is, the CO conversion rate is determined by the following formula (4).

$$\text{CO conversion rate} = \frac{(\text{synthesis gas-to-CO molar flow rate}) - (\text{off gas-to-CO molar flow rate})}{\text{synthesis gas-to-CO molar flow rate}} \times 100 \quad (4)$$

Further, because the FT synthesis reaction is an exothermic reaction, the reactor 30 is a heat-exchange-type reactor having the heat transfer tube 39 disposed inside the reactor 30. The reactor 30 is supplied, for example, with water (BFW: Boiler Feed Water) as a coolant so that the reaction heat of the above-described FT synthesis reaction can be recovered in the form of a middle-pressure steam by heat exchange between the slurry and the water.

Figure 2:
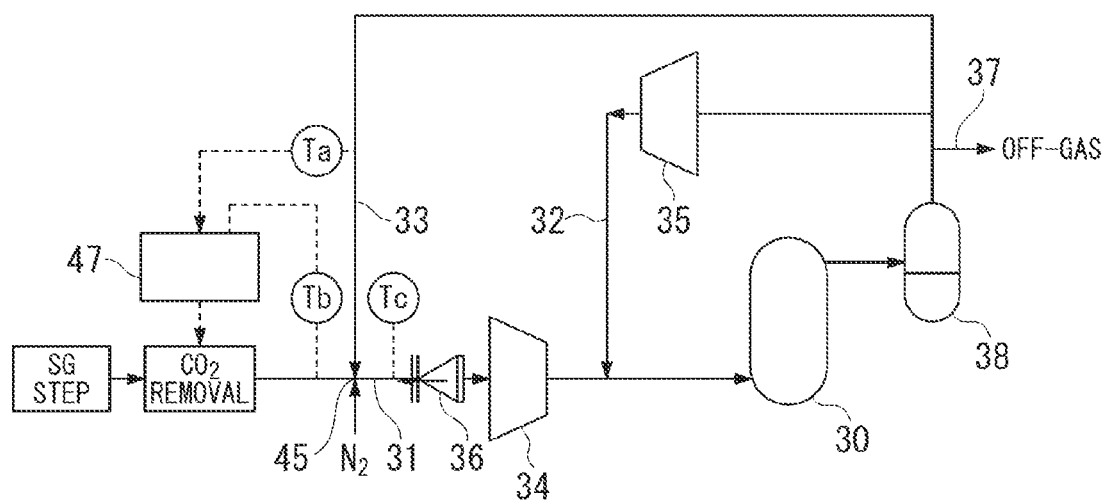
FIG. 2 is a systematic diagram which shows a schematic constitution of a hydrocarbon synthesis reaction apparatus shown in FIG. 1.

Still further, as the schematic constitution shown in FIG. 2, in addition to the reactor 30, the gas-liquid separator 38 and the off-gas discharge line 37, the FT synthesis unit 5 is provided with a synthesis gas supply line 31 in which a synthesis gas containing a carbon monoxide gas and a hydrogen gas as main components is sent by the synthesis gas production unit 3 (synthesis gas sending device) and the synthesis gas is compressed and supplied by the first compressor 34; a first recycle line 32 in which the unreacted synthesis gas after separation by the gas-liquid separator 38 is compressed and recycled into the reactor 30 by the second compressor 35; and a second recycle line 33 which recycles into the inlet side of the first compressor 34 a residual unreacted synthesis gas to be introduced into the first recycle line 32, a part of the unreacted synthesis gas after separation by the gas-liquid separator 38, at the time of start-up operation when the synthesis gas to be introduced from the synthesis gas production unit 3 into the reactor 30 is gradually increased in the introduction amount from a processing flow rate lower than a processing flow rate of the synthesis gas processed during operation at a rated flow rate (for example, 70% on the assumption that the processing flow rate during operation at a rated flow rate is given as 100%) to a processing flow rate of synthesis gas during operation at a rated flow rate (100% of the flow rate).

In this case, one of lines of an inert gas which is flowed within a system at the time of starting up the reactor 30 also functions as the second recycle line 33. Further, as shown in FIG. 2, when a suction strainer 36 is installed for removing foreign matter contained in an introduced gas at a site where the synthesis gas sent from the synthesis gas production unit 3 is introduced into the inlet side of the first compressor 34, on the upstream side of the suction strainer 36, there is installed a converging and mixing unit 45 at which the unreacted synthesis gas from the second recycle line 33 is converged and mixed with the synthesis gas sent by the synthesis gas production unit 3. Then, there is also installed a temperature controlling device 47 which controls the mixed gas mixed at the converging and mixing unit 45 in such a manner that a temperature Tc thereof is at least equal to or higher than a temperature Ta of the unreacted synthesis gas from the second recycle line 33.

Next is a description of the upgrading unit 7. The upgrading unit 7 includes, for example, a wax fraction hydrocracking reactor 50, a middle distillate hydrotreating reactor 52, a naphtha fraction hydrotreating reactor 54, gas-liquid separators 56, 58 and 60, a second fractionator 70, and a naphtha stabilizer 72. The wax fraction hydrocracking reactor 50 is connected to the bottom of the first fractionator 40. The middle distillate hydrotreating reactor 52 is connected to a middle section of the first fractionator 40. The naphtha fraction hydrotreating reactor 54 is connected to the top of the first fractionator 40. The gas-liquid separators 56, 58 and 60 are provided so as to correspond to the hydrogenation reactors 50, 52 and 54 respectively. The second fractionator 70 fractionally distills the liquid hydrocarbon compounds supplied from the gas-liquid separators 56 and 58. The naphtha stabilizer 72 rectifies the liquid hydrocarbon compounds within the naphtha fraction supplied from the gas-liquid separator 60 and fractionally distilled in the second fractionator 70. As a result, the naphtha stabilizer 72 discharges butane and components lighter than butane as an off-gas, and recovers components having a carbon number of five or greater as a naphtha product.

Next is a description of a process for synthesizing liquid fuels from a natural gas during operation at a rated flow rate (GTL process) using the liquid fuel synthesizing system 1 having the structure described above.

A natural gas (the main component of which is $CH_4$) is supplied as a hydrocarbon feedstock to the liquid fuel synthesizing system 1 from an external natural gas supply source (not shown in the drawing), such as a natural gas field or a natural gas plant. The above synthesis gas production unit 3 reforms the natural gas to produce a synthesis gas (a mixed gas containing carbon monoxide gas and hydrogen gas as main components).

Specifically, first, the natural gas described above is introduced to the desulfurization reactor 10 together with the hydrogen gas separated by the hydrogen separator 26. In the desulfurization reactor 10, sulfur components included in the natural gas are converted into hydrogen sulfide by the introduced hydrogen gas and the hydrodesulfurization catalyst. Further, in the desulfurization reactor 10, the produced hydrogen sulfide is absorbed and removed by a desulfurizing agent such as ZnO. By desulfurizing the natural gas in advance in this manner, reduction in the activity of the catalysts used in the reformer 12, the reactor 30 and so on, due to sulfur can be prevented.

The natural gas (which may also include carbon dioxide) that has been desulfurized in this manner is supplied to the reformer 12 after mixing with carbon dioxide gas ($CO_2$) supplied from a carbon dioxide supply source (not shown in the drawing) and the steam generated in the waste heat boiler 14. In the reformer 12, for example, the natural gas is reformed by the carbon dioxide gas and the steam via the aforementioned steam-carbon dioxide reforming process, thereby producing a high-temperature synthesis gas including carbon monoxide gas and hydrogen gas as main components. At this time, for example, a fuel gas and air for a burner installed in the reformer 12 are supplied to the reformer 12, and the combustion heat from the fuel gas in the burner is used to provide the necessary reaction heat for the above steam-carbon dioxide gas reforming reaction, which is an endothermic reaction.

The high-temperature synthesis gas (for example, 900° C., 2.0 MPaG) produced in the reformer 12 in this manner is supplied to the waste heat boiler 14, and is cooled (for example, to 400° C.) by heat exchange with the water flowing through the waste heat boiler 14, thereby recovering the waste heat from the synthesis gas.

At this time, the water heated by the synthesis gas in the waste heat boiler 14 is supplied to the gas-liquid separator 16. In the gas-liquid separator 16, the water that has been heated by the synthesis gas is separated into a high-pressure steam (for example, 3.4 to 10.0 MPaG) and water. The separated high-pressure steam is supplied to the reformer 12 or other external devices, whereas the separated water is returned to the waste heat boiler 14.

Meanwhile, the synthesis gas that has been cooled within the waste heat boiler 14 is supplied to either the absorption tower 22 of the $CO_2$ removal unit 20 or the reactor 30, after a condensed liquid fraction has been separated and removed from the synthesis gas in the gas-liquid separator 18. In the absorption tower 22, carbon dioxide gas contained in the synthesis gas is absorbed by an absorbent stored in the absorption tower 22, thereby removing the carbon dioxide gas from the synthesis gas. The absorbent that has absorbed the carbon dioxide gas within the absorption tower 22 is discharged from the absorption tower 22 and introduced into the regeneration tower 24. This absorbent that has been introduced into the regeneration tower 24 is then heated, for example, with steam, and subjected to a stripping treatment to strip the carbon dioxide gas. The striped carbon dioxide gas is discharged from the regeneration tower 24 and introduced into the reformer 12, where it can be reused for the above reforming reaction.

The synthesis gas produced in the synthesis gas production unit 3 in this manner is supplied to the reactor 30 of the above FT synthesis unit 5. At this time, the composition ratio of the synthesis gas supplied to the reactor 30 is adjusted to a composition ratio suitable for the FT synthesis reaction (for example, $H_2$:CO=2:1 (molar ratio)). In addition, the synthesis gas supplied to the reactor 30 is pressurized to a pressure suitable for the FT synthesis reaction (for example, approximately 3.6 MPaG) by the first compressor 34 provided in the line connecting the $CO_2$ removal unit 20 with the reactor 30.

Furthermore, a portion of the synthesis gas that has undergone separation of the carbon dioxide gas by the above $CO_2$ removal unit 20 is also supplied to the hydrogen separator 26. In the hydrogen separator 26, the hydrogen gas contained in the synthesis gas is separated by adsorption and desorption utilizing a pressure difference (hydrogen PSA) as described above. The separated hydrogen gas is supplied continuously from a gas holder or the like (not shown in the drawing) via a compressor (not shown in the drawing) to the various hydrogen-utilizing reactors (for example, the desulfurization reactor 10, the wax fraction hydrocracking reactor 50, the middle distillate hydrotreating reactor 52, the naphtha fraction hydrotreating reactor 54 and so on) within the liquid fuel synthesizing system 1 that performs predetermined reactions using hydrogen.

Next, the FT synthesis unit 5 synthesizes liquid hydrocarbon compounds by the FT synthesis reaction from the synthesis gas produced in the above synthesis gas production unit 3.

Specifically, the synthesis gas that has undergone separation of the carbon dioxide gas by the above $CO_2$ removal unit 20 is introduced into the reactor 30, and flows through the slurry including the catalyst contained in the reactor 30. During this time within the reactor 30, the carbon monoxide and hydrogen gas contained in the synthesis gas react with each other by the aforementioned FT synthesis reaction, and hydrocarbon compounds are produced. Moreover, during this FT synthesis reaction, the reaction heat of the FT synthesis reaction is recovered by the water flowing through the heat transfer tube 39 of the reactor 30, and the water that has been heated by this reaction heat is vaporized into steam. This steam is supplied to the gas-liquid separator 40 and separated into condensed water and a gas fraction. The water is returned to the heat transfer tube 39, while the gas fraction is supplied to an external device as a middle-pressure steam (for example, 1.0 to 2.5 MPaG).

The liquid hydrocarbon compounds synthesized in the reactor 30 in this manner are discharged from the middle section of the reactor 30 as a slurry that includes catalyst particles, and this slurry is introduced into the separator 41. In the separator 41, the introduced slurry is separated into the catalyst (the solid fraction) and a liquid fraction containing the liquid hydrocarbon compounds. A portion of the separated catalyst is returned to the reactor 30, whereas the liquid fraction is introduced into the first fractionator 42. Gaseous by-products, including unreacted synthesis gas from the FT synthesis reaction and gaseous hydrocarbon compounds produced in the FT synthesis reaction, are discharged from the top of the reactor 30. The gaseous by-products discharged from the reactor 30 are introduced into the gas-liquid separator 38. In the gas-liquid separator 38, the introduced gaseous by-products are cooled and separated into condensed liquid hydrocarbon compounds and a gas fraction. The separated liquid hydrocarbon compounds are discharged from the gas-liquid separator 38 and introduced into the first fractionator 42.

The separated gas fraction is discharged from the gas-liquid separator 38, with a portion of the gas fraction being reintroduced into the reactor 30. In the reactor 30, the unreacted synthesis gases (CO and $H_2$) contained in the reintroduced gas fraction are reused for the FT synthesis reaction. Further, a portion of the gas fraction which has been discharged from the gas-liquid separator 38 is discharged from the off-gas discharge line 37 outside the system as an off-gas and used as a fuel, or fuels equivalent to LPG (Liquefied Petroleum Gas) may be recovered from this gas fraction.

In the first fractionator 42, the liquid hydrocarbon compounds (with various carbon numbers) supplied from the reactor 30 via the separator 41 and the gas-liquid separator 38 in the manner described above are fractionally distilled into a naphtha fraction (with a boiling point that is lower than approximately 150° C.), a middle distillate (with a boiling point of approximately 150 to 360° C.) and a wax fraction (with a boiling point that exceeds approximately 360° C.). The liquid hydrocarbon compounds of the wax fraction (mainly $C_{22}$ or higher) discharged from the bottom of the first fractionator 42 are introduced into the wax fraction hydrocracking reactor 50. The liquid hydrocarbon compounds of the middle distillate equivalent to kerosene and gas oil (mainly $C_{11}$ to $C_{21}$) discharged from the middle section of the first fractionator 42 are introduced into the middle distillate hydrotreating reactor 52. The liquid hydrocarbon compounds of the naphtha fraction (mainly $C_5$ to $C_{10}$) discharged from the top of the first fractionator 42 are introduced into the naphtha fraction hydrotreating reactor 54.

The wax fraction hydrocracking reactor 50 hydrocracks the liquid hydrocarbon compounds of the high-carbon number wax fraction (hydrocarbons of approximately $C_{22}$ or higher) discharged from the bottom of the first fractionator 42 by using the hydrogen gas supplied from the above-described hydrogen separator 26 to reduce the carbon number to 21 or less. In this hydrocracking reaction, C—C bonds of hydrocarbon compounds with a large carbon number are cleaved. This process converts the hydrocarbon compounds with a large carbon number to hydrocarbon compounds with a small carbon number. Further, in the wax fraction hydrocracking reactor 50, the reaction for hydroisomerizing linear saturated hydrocarbon compounds (normal paraffins) to produce branched saturated hydrocarbon compounds (isoparaffins) proceeds in parallel with the hydrocracking reaction. This improves the low-temperature fluidity of the wax fraction hydrocracked product, which is a required property for a fuel oil base stock. Moreover, in the wax fraction hydrocracking reactor 50, a hydrodeoxygenation reaction of oxygen-containing compounds such as alcohols, and a hydrogenation reaction of olefins, both of which may be contained in the wax fraction that functions as the feedstock, also proceed during the hydrocracking process. The products including the liquid hydrocarbon compounds hydrocracked and discharged from the wax fraction hydrocracking reactor 50 are introduced into the gas-liquid separator 56, and separated into a gas and a liquid. The separated liquid hydrocarbon compounds are introduced into the second fractionator 70, and the separated gas fraction (which includes hydrogen gas) is introduced into the middle distillate hydrotreating reactor 52 and the naphtha fraction hydrotreating reactor 54.

In the middle distillate hydrotreating reactor 52, the liquid hydrocarbon compounds of the middle distillate equivalent to kerosene and gas oil, which have a mid-range carbon number (of approximately $C_{11}$ to $C_{21}$) and have been discharged from the middle section of the first fractionator 42, are hydrotreated. In the middle distillate hydrotreating reactor 52, hydrogen gas supplied from the hydrogen separator 26 via the wax fraction hydrocracking reactor 50 is used for the hydrotreating. In this hydrotreating reaction, olefins contained in the above liquid hydrocarbon compounds are hydrogenated to produce saturated hydrocarbon compounds, and oxygen-containing compounds such as alcohols contained in the liquid hydrocarbon compounds are hydrodeoxygenated and converted into saturated hydrocarbon compounds and water. Moreover, in this hydrotreating reaction, a hydroisomerization reaction that isomerizes linear saturated hydrocarbon compounds (normal paraffins) and converts them into branched saturated hydrocarbon compounds (isoparaffins) also proceeds, thereby improving the low-temperature fluidity of the product oil, which is a required property for a fuel oil. The product including the hydrotreated liquid hydrocarbon compounds is separated into a gas and a liquid in the gas-liquid separator 58.

The separated liquid hydrocarbon compounds are introduced into the second fractionator 70, and the separated gas fraction (which includes hydrogen gas) is reused for the above hydrogenation reaction.

In the naphtha fraction hydrotreating reactor 54, the liquid hydrocarbon compounds of the naphtha fraction, which have a low carbon number (approximately $C_{10}$ or less) and have been discharged from the top of the first fractionator 42, are hydrotreated. In the naphtha fraction hydrotreating reactor 54, hydrogen gas supplied from the hydrogen separator 26 via the wax fraction hydrocracking reactor 50 is used for the hydrotreating. In the naphtha fraction hydrotreating reaction, the hydrogenation of olefins and hydrodeoxygenation of oxygen-containing compounds such as alcohols mainly proceed. The product including hydrotreated liquid hydrocarbon compounds is separated into a gas and a liquid in the gas-liquid separator 60. The separated liquid hydrocarbon compounds are introduced into the naphtha stabilizer 72, and the separated gas fraction (which includes hydrogen gas) is reused for the above hydrogenation reaction.

In the second fractionator 70, the liquid hydrocarbon compounds supplied from the wax fraction hydrocracking reactor 50 and the middle distillate hydrotreating reactor 52 in the manner described above are fractionally distilled into hydrocarbon compounds with a carbon number of $C_{10}$ or less (with boiling points lower than approximately 150° C.), a kerosene fraction (with a boiling point of approximately 150 to 250° C.), a gas oil fraction (with a boiling point of approximately 250 to 360° C.) and an uncracked wax fraction (with a boiling point exceeding approximately 360° C.) from the wax fraction hydrocracking reactor 50. The uncracked wax fraction is obtained from the bottom of the second fractionator 70, and this is recycled to a position upstream of the wax fraction hydrocracking reactor 50. Kerosene and gas oil are discharged from the middle section of the second fractionator 70. Meanwhile, hydrocarbon compounds of $C_{10}$ or less are discharged from the top of the second fractionator 70 and introduced into the naphtha stabilizer 72.

In the naphtha stabilizer 72, the hydrocarbon compounds of $C_{10}$ or less, which have been supplied from the naphtha fraction hydrotreating reactor 54 and fractionally distilled in the second fractionator 70, are distilled, and naphtha ($C_5$ to $C_{10}$) is obtained as a product. Accordingly, high-purity naphtha is discharged from the bottom of the naphtha stabilizer 72. Meanwhile, an off-gas including mainly hydrocarbon compounds with a predetermined carbon number or less ($C_4$ or less), which is not a targeted product, is discharged from the top of the naphtha stabilizer 72. This off-gas is used as a fuel gas, or alternatively, a fuel equivalent to LPG may be recovered from the off-gas.

Next is a description of a start-up process of the FT synthesis unit 5.

Here, the first compressor 34 and the second compressor 35 are set to be substantially the same in capacity. On the assumption that the reactor 30 has a processing flow rate of 100 when operated at a rated flow rate, each of the first compressor 34 and the second compressor 35 shares and takes charge of a flow rate of each 50. Therefore, for example, where the reactor 30 is operated at a 70% load, the first compressor 34 is to be operated at a flow rate of 35 (50×0.7=35) under the condition that the reactor 30 is operated at a rated processing flow rate of 100. Where the compressor is operated in a capacity lower than the rated capacity, there is mainly employed a so-called a spillback method in which the outlet side of the compressor is returned to the inlet side thereof. Therefore, where the compressor is operated at a flow rate of 70%, spillback is carried out at 30%, with the compressor actually operated at a full capacity of 100%.

Figure 3:
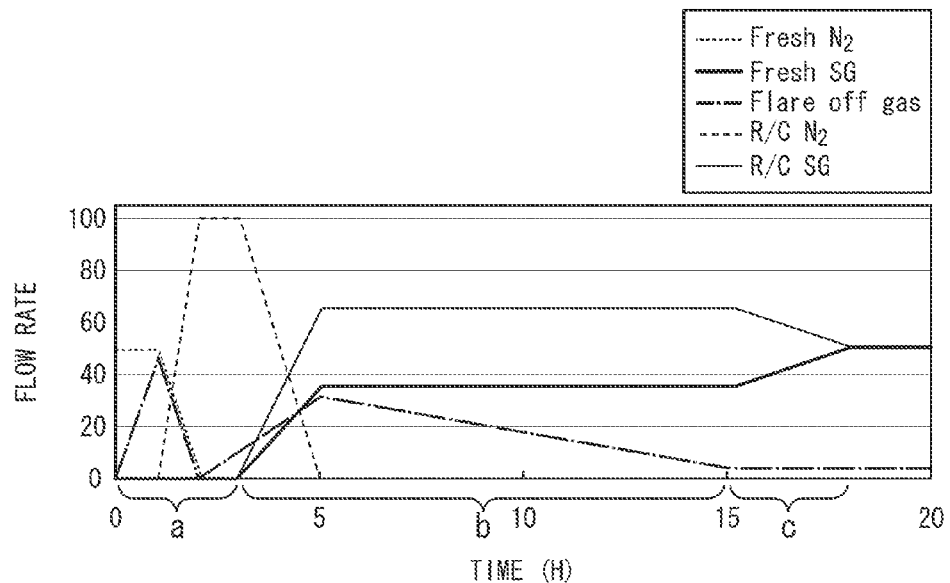
FIG. 3 is a characteristic diagram which shows changes in flow rate of each gas when a start-up process of the embodiment in the present invention is performed by using the apparatus of FIG. 2.
Figure 4:
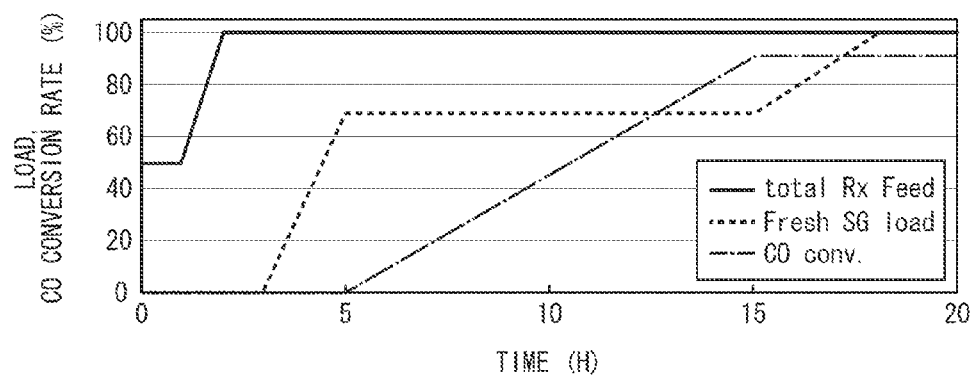
FIG. 4 is a characteristic diagram which shows load percentages of a synthesis gas (SG), the total change in flow rate of a reactor, and the CO conversion rate when the start-up process of the embodiment in the present invention is performed by the apparatus of FIG. 2.
Figure 5:
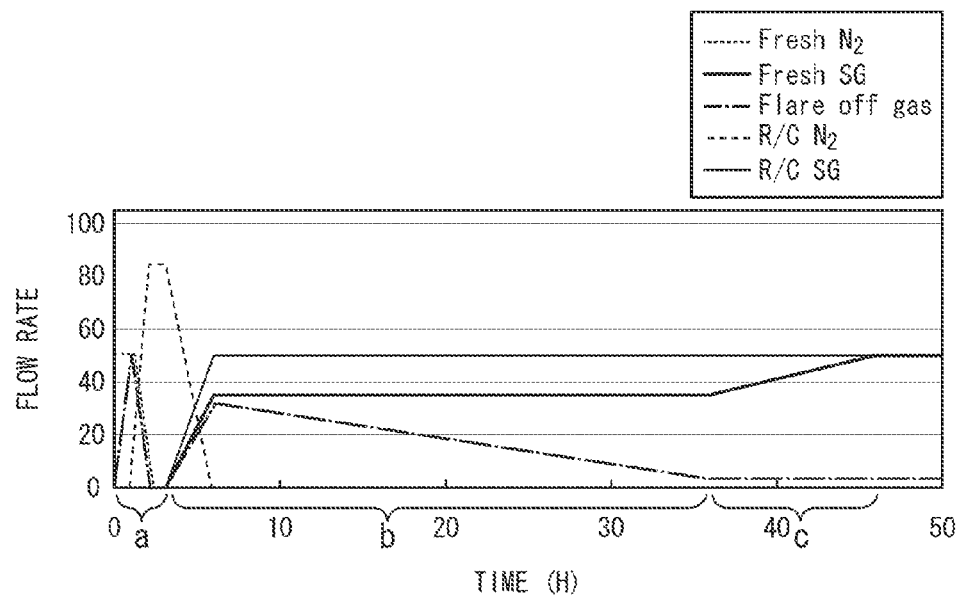
FIG. 5 is a characteristic diagram which shows a comparative example of FIG. 3.
Figure 6:
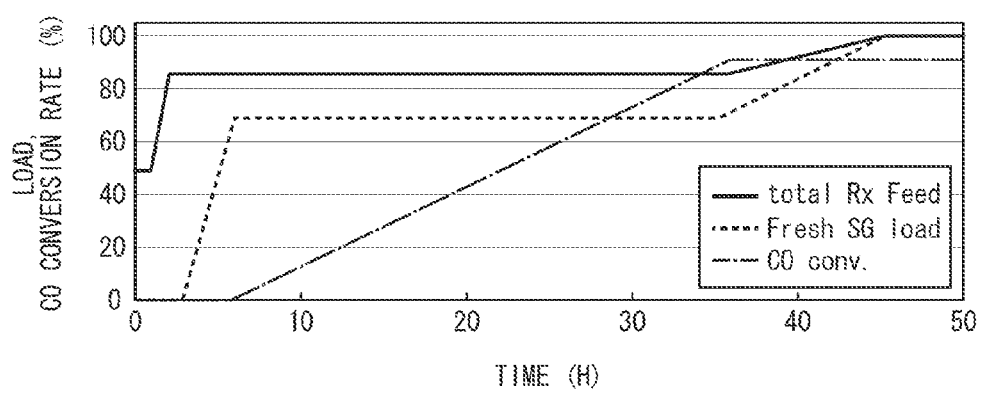
FIG. 6 is a characteristic diagram which shows a comparative example of FIG. 4.
Figure 7:
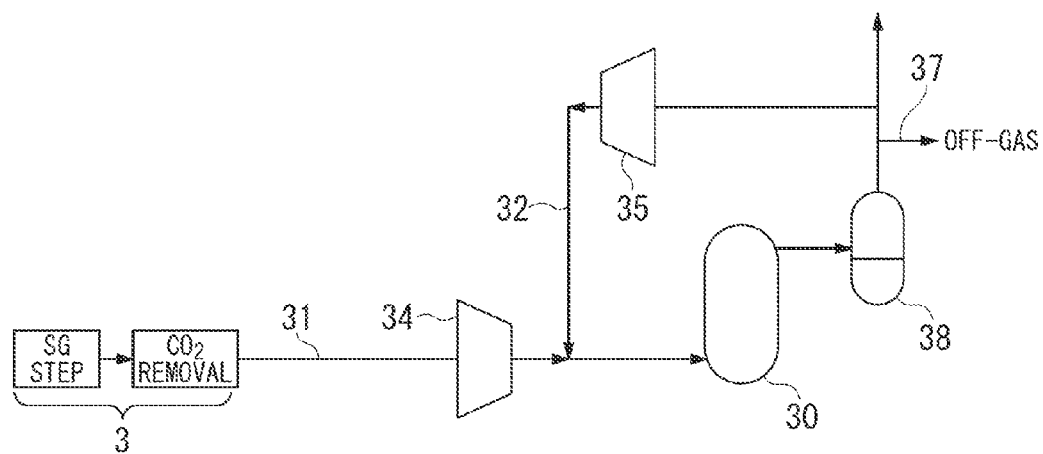
FIG. 7 is a systematic diagram which shows a schematic constitution of a conventional hydrocarbon synthesis reaction apparatus.

Next is a description of operation at the time of start-up and change in flow rate and so on. FIG. 3 is a characteristic diagram which shows a change in flow rate of each gas where there is performed the start-up process of one embodiment of the present invention. FIG. 4 is a characteristic diagram which shows the percentage of loads of the synthesis gas (SG) at that time, changes in total flow rate of the reactor, and the CO conversion rate. Further, FIG. 5 is a characteristic diagram which shows a comparative example with respect to FIG. 3. FIG. 6 is a characteristic diagram which shows a comparative example with respect to FIG. 4.

As shown in FIG. 3, at the time of start-up, prior to introduction of the synthesis gas into the reactor 30, as a first step, nitrogen gas (Fresh N2) is introduced in advance into the reactor 30 through the synthesis gas supply line 31. The first compressor 34 and the second compressor 35 are both operated at a rated flow rate (operated at the flow rate of 100 (50+50)), and the nitrogen gas is flowed via the first recycle line 32 and the second recycle line 33, by which a gas inside a system is replaced with the nitrogen gas, with an off gas being discharged through the off-gas discharge line 37, and a catalyst slurry inside the reactor 30 is fluidized (a part indicated with a shown in FIG. 3).

Next, as a second step, the synthesis gas (Fresh SG) is introduced at a flow rate (for example, 35) lower than a processing flow rate (50) during operation at a rated flow rate through the synthesis gas supply line 31, in a state where the first compressor 34 is operated at a rated flow rate (100% operation=flow rate of 50), into the reactor 30 which is in a state that the catalyst slurry is fluidized by performing the first step. An unreacted synthesis gas which has been discharged from the reactor 30 and separated by the gas-liquid separator 38 is flowed via the first recycle line 32 by operating the second compressor 35 at a rated flow rate (100% operation=flow rate of 50). In addition, a residual unreacted synthesis gas (flow rate of 15) which is introduced into the first recycle line 32, of the unreacted synthesis gas after separation by the gas-liquid separator 38, is flowed into the inlet side of the first compressor 34 which is operated at a rated flow rate via the second recycle line 33. In the drawing, the unreacted synthesis gas is indicated as R/C SG. Thereby, the gas inside the system is replaced with the synthesis gas, with the off gas discharged through the off gas discharge line 37, and the supply flow rate of the synthesis gas from the synthesis gas supply line 31 is maintained at a constant flow rate (35) which is lower than a processing flow rate during operation at a rated flow rate. Further, in the meantime, the reactor 30 is gradually increased in temperature, by which the CO conversion rate is also raised (which is a part indicated with b in FIG. 3).

Next, as a third step, at a stage where the reaction becomes stable in the second step, the synthesis gas to be introduced into the reactor 30 through the synthesis gas supply line 31 is gradually increased in flow rate, and the unreacted synthesis gas to be flowed through the second recycle line 33 is gradually decreased in flow rate. Finally, the flow rate of the synthesis gas to be introduced into the reactor 30 through the synthesis gas supply line 31 is increased up to the processing flow rate (50) of the synthesis gas which is processed during operation at a rated flow rate (a part indicated with c in FIG. 3). Thereafter, the shift can be made to operate at a rated flow rate.

Next is a description of a comparative example.

As shown in FIG. 5, in the first step of the comparative example, prior to introduction of the synthesis gas into the reactor 30, a fresh nitrogen gas (Fresh N2) is in advance introduced into the reactor 30 through the synthesis gas supply line 31. The first compressor 34 is operated at 70% (flow rate of 35) and the second compressor 35 is operated at a rated flow rate (flow rate of 50) to flow the nitrogen gas via the first recycle line 32 and the second recycle line 33. Thereby, the gas inside the system is replaced with the nitrogen gas, with the off gas discharged from the off-gas discharge line 37, and the catalyst slurry inside the reactor 30 is also fluidized. In this case, the nitrogen gas (R/C N2) to be recycled is flowed at a flow rate of 85 (a part indicated with a in FIG. 5).

Next, as the second step, a fresh synthesis gas (Fresh SG) is introduced at a flow rate of 35 through the synthesis gas supply line 31 into the reactor 30 which is in a state that a catalyst slurry is fluidized by performing the first step, with the first compressor 34 operated at 70%. The unreacted synthesis gas (RIC SG) which has been discharged from the reactor 30 and separated by the gas-liquid separator 38 is flowed via the first recycle line 32 by operating the second compressor 35 at a rated flow rate (operation at 100%). Upon starting introduction of the synthesis gas, a suctioned gas of the first compressor 34 is totally converted to a synthesis gas. Therefore, the gas flow rate from the second recycle line 33 becomes zero. Then, the above-described operation is carried out, by which the gas inside the system is replaced with the synthesis gas, with the off gas discharged through the off-gas discharge line 37, and the flow rate of supplying the synthesis gas from the synthesis gas supply line 31 is maintained at a constant flow rate of 35 which is lower than a processing flow rate during operation at a rated flow rate. Further, in the meantime, the reactor 30 is gradually increased in temperature, and the CO conversion rate is increased accordingly (a part indicated with b in FIG. 5).

Next, as a third step, at a stage where the reaction becomes stable in the second step, the synthesis gas to be introduced into the reactor 30 through the synthesis gas supply line 31 is gradually increased in flow rate, and finally the flow rate of the synthesis gas to be introduced into the reactor 30 through the synthesis gas supply line 31 is increased up to a processing flow rate (50) of the synthesis gas which is treated during operation at a rated flow rate (a part indicated with c in FIG. 5). Thereafter, the shift can be made to operate at a rated flow rate.

When the above-described operation is conducted, a total introduction gas amount to be introduced into the reactor 30 (total Rx Feed), an introduction amount of fresh synthesis gas (Fresh SG load) and a CO conversion rate (CO Conv.) are changed as shown in FIG. 4, and FIG. 6.

As so far described, according to the embodiment of the present invention, nitrogen gas at the time of start-up is flowed via the first recycle line 32 and the second recycle line 33 by operating the first compressor 34 and the second compressor 35 at a rated flow rate (50+50). Thereby, the shift can be made to introduce the synthesis gas as a next stage, with a fluid state inside the reactor 30 kept stable. Further, when and after the shift has been made to introduce the synthesis gas, a mixed gas containing the synthesis gas and the unreacted synthesis gas can be introduced into the reactor 30 at the rated flow rate by operating the first compressor 34 at the rated flow rate. That is, the flow rate (35) of the synthesis gas which flows into the first compressor 34 is added to the flow rate (15) from the second recycle line 33 to provide a flow rate of 50, and the flow rate of 50 from the first recycle line 32 is added thereto, by which gas is introduced at a sufficiently required flow rate of 100 which is equivalent to the rated flow rate. Therefore, a stable fluid state can be kept inside the reactor 30. Thereby, with substantially no consideration given to influences by the fluid state, the reactor 30 is gradually increased in temperature, and the reactivity (conversion rate) is raised accordingly. Further, the flow rate of the synthesis gas can be safely increased up to the rated flow rate. Therefore, events which require care and monitoring at the time of start-up are decreased to facilitate the operation.

Still further, as compared with the comparative example, the fluid state can be kept constant all the time inside the reactor 30, by which the period of time required for shifting to operation at a rated safe flow rate can be greatly shortened (the time can be shortened to approximately 17 hours, whereas approximately 46 hours were required in the comparative example). Still further, since the first compressor 34 which compresses the synthesis gas can be fully utilized for the performance without operating at a low flow rate, it is possible to increase efficiency.

Further, the introduction amount of the synthesis gas to be introduced into the reactor 30 is kept at a low flow rate confirmed the safety thereof in advance, the reactor 30 is gradually increased in temperature, while the stability of the reaction is confirmed, thereby raising the reactivity (conversion rate), and an unreacted synthesis gas can be introduced through the second recycle line 33 into the inlet side of the first compressor 34 which compresses the synthesis gas at the time of start-up operation when it is necessary to increase the flow rate of the synthesis gas up to a rated flow rate.

Therefore, the unreacted synthesis gas can be used to supplement a shortage of the flow rate with respect to a rated flow rate of the synthesis gas when the first compressor 34 is operated at the rated flow rate.

That is, for example, at the start-up operation in which there is no choice but to start the operation by introducing the synthesis gas at a low flow rate in order to prevent the reaction from going out of control, the first compressor 34 is operated at the rated flow rate, and a mixed gas containing the synthesis gas and the unreacted synthesis gas is introduced at the rated flow rate into the reactor 30, thus making it possible to maintain a stable fluid state inside the reactor 30. Thereby, with substantially no consideration given to influences by the fluid state, the reactor 30 is gradually increased in temperature to raise the reactivity (conversion rate), and the flow rate of the synthesis gas can be safely increased up to the rated flow rate.

Further, the line which is used as a flow line of an inert gas is also used as the second recycle line 33 for cycling the unreacted synthesis gas. Therefore, it is possible to utilize the facilities to the maximum extent and suppress an increase in cost.

Further, the temperature of gas after mixture of the synthesis gas with the unreacted synthesis gas is controlled so as to be equal to or higher than the temperature of the unreacted synthesis gas during recycle operation of the unreacted synthesis gas. Thereby, it is possible to prevent any trouble resulting from condensation of a trace amount of oil content contained in the unreacted synthesis gas. As a result, it is possible to guarantee stable operation of the first compressor 34.

Hereafter, a description will be given by use of a specific example.

In order to stabilize the fluidity inside the reactor 30, where the second recycle line 34 is used to recycle the unreacted synthesis gas into the inlet side of the first compressor 34, the temperature of the synthesis gas is 33° C., the temperature of the unreacted synthesis gas is 34° C., and the temperature of the gas after mixture is 33° C. Immediately after start of operation, a monitoring pressure of the suction strainer 36 is gradually increased to cause operational troubles. Therefore, an amine solution for absorbing carbon dioxide gas in the $CO_2$ removal step is increased in temperature, by which the temperature of the synthesis gas is increased to 38° C. Then, the temperature of the gas after mixture is also increased to 38° C. The monitoring pressure of the suction strainer 36 is returned to a substantially normal value, which allows the operation to continue.

Where a temperature Tb of the synthesis gas is lower than a temperature Ta of the unreacted synthesis gas which is cycling, mixture of the synthesis gas with the unreacted synthesis gas may result in condensation of oil content which is contained at a trace amount in the unreacted synthesis gas. Attachment of the condensed oil content on the suction strainer of the compressor will gradually clog the strainer. As a result, the monitoring pressure of the strainer is increased with lapse of time to disable stable operation of the compressor. Thereby, it is difficult to stably secure a flow velocity of gas necessary for cycling via the second recycle line 34. Thus, the temperature Tc of the synthesis gas after mixture is set higher than the temperature Ta of the unreacted synthesis gas in cycling to carry out operation in such a manner that the oil contained in trace amounts in the unreacted synthesis gas will not undergo condensation due to decrease in temperature upon mixture of the unreacted synthesis gas in cycling with the synthesis gas.

For example, in order to prevent reduction in the amount of gas to be introduced into the reactor 30 due to decrease in acid-gas absorbing capacity of amines and in suction amount of the compressor in the $CO_2$ removal step, the temperature of the synthesis gas is set constantly higher by 2 to 5° C. than the temperature of the gas in cycling to carry out operation. Thereby, the temperature of a mixed gas when they are mixed is made higher than that of the unreacted synthesis gas, thus eliminating a possibility that the oil contained in trace amounts in the unreacted synthesis gas may undergo condensation. As a result, it is possible to stably operate the compressor during recycle operation.

However, if the rise increase range of the gas temperature after mixture is small, condensation of the oil is insufficiently prevented. If the rise increase range of the gas temperature after mixture is excessively large, the compressor is decreased in suction amount resulting in reduced amount of the gas to be introduced into the reactor 30. Further, the acid-gas absorbing capacity of amine solution is decreased to result in a failure of meeting the required performance. Thus, the temperature is set so as to be higher in a range of approximately 2 to 5° C. It is, thereby, possible to balance both preventing the suction strainer 36 of the compressor from being clogged and providing the acid-gas absorbing capacity of an amine solution.

As a result, it is possible to prevent condensation of the oil in the suction strainer 36 of the compressor and also operate the compressor 34 stably for a long time. Further, since the compressor 34 is operated stably for a long period of time, it is possible to maintain a fluid state inside the reactor 30 stable and produce GTL (Gas to Liquid) oil stably.

There may be selected any method for increasing the temperature of the synthesis gas after mixture. Further, the temperature controlling device is provided in such a manner that the temperature of the synthesis gas before mixture with the unreacted synthesis gas is not increased but the temperature of the mixed gas is finally made higher than that of the unreacted synthesis gas, thus making it possible to solve the problem of condensation of the oil.

Further, in the above-described embodiment, the present invention has been described by exemplifying the start-up process of the hydrocarbon synthesis reaction apparatus. The present invention shall not be limited thereto but may be applicable to a case where the FT synthesis unit is operated, with low loads being kept, when the amount of the synthesis gas to be introduced into the reactor is required to be at a rate lower than a rated flow rate for some reason and a case where the flow rate of the synthesis gas is gradually increased from the above state to the rated flow rate.

INDUSTRIAL APPLICABILITY

The present invention relates to a hydrocarbon synthesis reaction apparatus, a start-up process thereof, and a hydrocarbon synthesis reaction system. The present invention is able to start-up the system in a short time, while securing a stable fluid state of a catalyst and reaction conditions.

DESCRIPTION OF THE REFERENCE SIGNS

3: Synthesis gas production unit (synthesis gas sending device)
5: FT synthesis unit (hydrocarbon synthesis reaction apparatus)
7: Upgrading unit (product fractionating unit)
30: Reactor
31: Synthesis gas supply line 32: First recycle line
33: Second recycle line
34: First compressor
35: Second compressor
36: Suction strainer
37: Off-gas discharge line
38: Gas-liquid separator

The invention claimed is:

1. A hydrocarbon synthesis reaction apparatus comprising:
   a synthesis gas supply line in which a synthesis gas containing carbon monoxide gas and hydrogen gas as main components is sent by a synthesis gas sending device and the thus sent synthesis gas is compressed and supplied by a first compressor;
   a reactor configured to accommodate a catalyst slurry prepared by suspending solid catalyst particles in a liquid to synthesize hydrocarbons by bringing the synthesis gas supplied from the synthesis gas supply line into contact with the catalyst slurry;
   a gas-liquid separator configured to separate an unreacted synthesis gas and hydrocarbons discharged from the reactor into a gas and a liquid;
   an off-gas discharge line configured to discharge a portion of gas after separation by the gas-liquid separator as an off gas outside a system;
   a first recycle line in which the unreacted synthesis gas after separation by the gas-liquid separator is compressed and recycled into the reactor by a second compressor; and
   a second recycle line configured to recycle into the inlet side of the first compressor a residual unreacted synthesis gas to be introduced into the first recycle line, a part of the unreacted synthesis gas after separation by the gas-liquid separator, at the time of start-up operation when the synthesis gas to be introduced from the synthesis gas sending device to the reactor is introduced in a gradually increasing amount from a processing flow rate lower than the processing flow rate of the synthesis gas to be processed during operation at a rated flow rate to a processing flow rate of the synthesis gas during operation at a rated flow rate.

2. The hydrocarbon synthesis reaction apparatus according to claim 1, wherein
   the hydrocarbon synthesis reaction apparatus is provided with the first recycle line, and an inert gas flow line which is communicated with the inlet side of the first compressor from the gas-liquid separator, the first recycle line and the inlet gas flow line serve as an inert gas flow line in which a gas inside a system is replaced with an inert gas at the time of starting up the reactor and the catalyst slurry is also fluidized, and wherein
   the inert gas flow line is also used as the second recycle line.

3. The hydrocarbon synthesis reaction apparatus according to claim 1 further comprising:
   a converging and mixing unit which is installed at an upstream side at a site where the synthesis gas sent from the synthesis gas sending device is introduced into the inlet side of the first compressor and in which the unreacted synthesis gas from the second recycle line is converged and mixed with the synthesis gas sent from the synthesis gas sending device; and
   a temperature controlling device configured to control a mixed gas mixed by the converging and mixing unit in such a manner that a temperature thereof is made at least equal to or higher than a temperature of the unreacted synthesis gas from the second recycle line.

4. A hydrocarbon synthesis reaction system for producing a liquid fuel base stock from a hydrocarbon feedstock, the hydrocarbon synthesis reaction system comprising:
   the hydrocarbon synthesis reaction apparatus according to claim 1; and
   a product fractionating unit configured to fractionate a liquid fuel base stock from hydrocarbons produced by the hydrocarbon synthesis reaction apparatus, wherein
   the synthesis gas sending device is a synthesis gas production unit configured to reform the hydrocarbon feedstock to produce the synthesis gas and sends the synthesis gas to the synthesis gas supply line.

5. A start-up process of a hydrocarbon synthesis reaction apparatus described in claim 1, the start-up process comprising:
   a first step in which, prior to introduction of the synthesis gas into the reactor, an inert gas is introduced into the reactor in advance through the synthesis gas supply line, the first compressor and the second compressor are both operated at a rated flow rate to flow the inert gas via the first recycle line and the second recycle line, thereby, a gas inside a system is replaced with the inert gas, with the off gas discharged from the off-gas discharge line, and also the catalyst slurry is fluidized;
   a second step in which the synthesis gas is introduced through the synthesis gas supply line, with the first compressor operated at a rated flow rate, into the reactor which is in a state that the catalyst slurry is fluidized by performing the first step at a flow rate lower than a processing flow rate during operation at a rated flow rate, an unreacted synthesis gas discharged from the reactor and separated by the gas-liquid separator is flowed via the first recycle line by operating the second compressor at a rated flow rate, and also a residual unreacted synthesis gas to be introduced into the first recycle line, a part of the unreacted synthesis gas after separation by the gas-liquid separator, is flowed via the second recycle line into the inlet side of the first compressor operated at a rated flow rate, thereby, the gas inside the system is replaced with the synthesis gas, with the off gas discharged from the off-gas discharge line, and the flow rate of supplying the synthesis gas from the synthesis gas supply line is also maintained at a constant flow rate lower than a processing flow rate during operation at a rated flow rate; and
   a third step in which, at a stage that reaction becomes stable in the second step, the synthesis gas to be introduced into the reactor through the synthesis gas supply line is gradually increased in flow rate, while the unreacted synthesis gas to be flowed through the second recycle line is gradually decreased in flow rate, and the flow rate of the synthesis gas to be finally introduced into the reactor through the synthesis gas supply line is increased up to the processing flow rate of the synthesis gas which is processed during operation at a rated flow rate.

* * * * *